(12) United States Patent
Nakagawa et al.

(10) Patent No.: US 7,851,669 B2
(45) Date of Patent: Dec. 14, 2010

(54) FLEXIBLE ABSORBENT ARTICLE WITH IMPROVED BODY FIT (75) Inventors: Yasue Nakagawa, Bad Soden am Taunus (DE); Holger Beruda, Schwalbach am Taunus (DE); Mattias Schmidt, Idstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 305 days.

(21) Appl. No.: 11/493,406

(22) Filed: Jul. 26, 2006

(65) Prior Publication Data
US 2007/0027436 A1 Feb. 1, 2007

Related U.S. Application Data (60) Provisional application No. 60/702,437, filed on Jul. 26, 2005, provisional application No. 60/812,767, filed on Jun. 12, 2006.

(51) Int. Cl.
*A61F 13/15* (2006.01)
*A61F 13/20* (2006.01)

(52) U.S. Cl. .................... 604/378; 604/367; 604/368; 604/374

(58) Field of Classification Search ............... 604/378, 604/368
See application file for complete search history.

(56) References Cited

U.S. PATENT DOCUMENTS

| 3,860,003 | A | | 1/1975 | Buell |
| 4,610,678 | A | | 9/1986 | Weisman et al. |
| 4,673,402 | A | | 6/1987 | Weisman et al. |
| 4,699,619 | A | * | 10/1987 | Bernardin .................. 604/378 |
| 4,773,903 | A | | 9/1988 | Weisman et al. |
| 4,834,735 | A | | 5/1989 | Alemany et al. |
| 4,940,464 | A | | 7/1990 | Van Gompel et al. |
| 4,950,264 | A | | 8/1990 | Osborn, III |
| 5,092,861 | A | | 3/1992 | Nomura et al. |
| 5,102,597 | A | | 4/1992 | Roe et al. |
| 5,151,092 | A | | 9/1992 | Buell et al. |
| 5,246,433 | A | | 9/1993 | Hasse et al. |
| 5,260,345 | A | | 11/1993 | Desmarais et al. |

(Continued)

FOREIGN PATENT DOCUMENTS

EP    1 518 566 A1    3/2005

(Continued)

OTHER PUBLICATIONS

U.S. Appl. No. 11/493,404, filed Jul. 26, 2006, Nakagawa et al.

(Continued)

*Primary Examiner*—Tatyana Zalukaeva
*Assistant Examiner*—Susan Su
(74) *Attorney, Agent, or Firm*—Laura L. Whitmer; Amy M. Foust; Andrew A Paul (57) ABSTRACT An absorbent article that has a thin, conformable absorbent core where the core has at least two layers, each including a different superabsorbent material, and each being typically substantially free of cellulosic fibers, is described. The absorbent article has a Circular Bend Flexibility of less than about 15 N. The core includes a storage layer and an acquisition/storage layer each a specific basis capacity of and absorption efficiency.

8 Claims, 3 Drawing Sheets

U.S. PATENT DOCUMENTS

| | | | | |
|---|---|---|---|---|
| 5,338,766 A * | 8/1994 | Phan et al. | | 521/63 |
| 5,387,207 A | 2/1995 | Dyer et al. | | |
| 5,397,316 A | 3/1995 | Lavon | | |
| 5,411,497 A | 5/1995 | Tanzer et al. | | |
| 5,554,145 A | 9/1996 | Roe et al. | | |
| 5,562,646 A | 10/1996 | Goldman et al. | | |
| 5,569,234 A | 10/1996 | Buell et al. | | |
| 5,599,335 A | 2/1997 | Goldman et al. | | |
| 5,625,222 A | 4/1997 | Yoneda et al. | | |
| 5,762,641 A * | 6/1998 | Bewick-Sonntag et al. | | 604/378 |
| 5,836,929 A * | 11/1998 | Bewick-Sonntag et al. | | 604/368 |
| 5,855,571 A * | 1/1999 | Steger et al. | | 604/368 |
| 5,897,545 A | 4/1999 | Kline et al. | | |
| 5,938,650 A * | 8/1999 | Baer et al. | | 604/368 |
| 5,957,908 A | 9/1999 | Kline et al. | | |
| 6,004,306 A | 12/1999 | Robles et al. | | |
| 6,083,210 A | 7/2000 | Young et al. | | |
| 6,103,951 A * | 8/2000 | Freeman | | 602/48 |
| 6,103,953 A * | 8/2000 | Cree et al. | | 604/365 |
| 6,120,487 A | 9/2000 | Ashton | | |
| 6,120,489 A | 9/2000 | Johnson et al. | | |
| 6,278,037 B1 * | 8/2001 | Schmidt et al. | | 604/369 |
| 6,399,854 B1 * | 6/2002 | Vartiainen | | 604/367 |
| 6,673,981 B1 * | 1/2004 | Strombom et al. | | 604/368 |
| 6,844,066 B2 * | 1/2005 | Hamed | | 428/393 |
| 6,989,005 B1 | 1/2006 | Lavon et al. | | |
| 2001/0027302 A1 * | 10/2001 | Glaug et al. | | 604/378 |
| 2002/0091368 A1 | 7/2002 | Lavon et al. | | |
| 2002/0165288 A1 | 11/2002 | Frenz et al. | | |
| 2003/0149414 A1 * | 8/2003 | Mehawej | | 604/368 |
| 2003/0199844 A1 | 10/2003 | Lavon et al. | | |
| 2003/0233082 A1 | 12/2003 | Kline et al. | | |
| 2004/0024379 A1 | 2/2004 | Lavon et al. | | |
| 2004/0030314 A1 | 2/2004 | Lavon et al. | | |
| 2004/0039361 A1 | 2/2004 | Lavon et al. | | |
| 2004/0078015 A1 * | 4/2004 | Copat et al. | | 604/370 |
| 2004/0162536 A1 * | 8/2004 | Becker et al. | | 604/367 |
| 2004/0167486 A1 | 8/2004 | Busam et al. | | |
| 2004/0193129 A1 * | 9/2004 | Guidotti et al. | | 604/378 |
| 2005/0070867 A1 | 3/2005 | Beruda et al. | | |
| 2005/0101928 A1 | 5/2005 | Beruda et al. | | |
| 2005/0119632 A1 | 6/2005 | Sierra et al. | | |
| 2005/0215965 A1 * | 9/2005 | Schmidt et al. | | 604/358 |
| 2005/0222547 A1 | 10/2005 | Beruda et al. | | |
| 2005/0234410 A1 | 10/2005 | Ashton et al. | | |
| 2006/0141891 A1 * | 6/2006 | Melius et al. | | 442/416 |
| 2006/0229582 A1 | 10/2006 | Lavon | | |
| 2007/0027435 A1 | 2/2007 | Nakagawa et al. | | |

FOREIGN PATENT DOCUMENTS

| | | |
|---|---|---|
| WO | WO 94/10957 A1 | 5/1994 |
| WO | WO 97/12575 A1 | 4/1997 |
| WO | WO 01/24756 A1 | 4/2001 |
| WO | WO 03/043670 A1 | 5/2003 |
| WO | WO 2004/071363 A1 | 8/2004 |
| WO | WO 2004/105666 A1 | 12/2004 |
| WO | WO 2005/014066 A1 | 2/2005 |
| WO | WO 2005/016208 A1 | 2/2005 |
| WO | WO 2005/097025 A1 | 10/2005 |

OTHER PUBLICATIONS

International Search Report, Nov. 6, 2006.

* cited by examiner

FLEXIBLE ABSORBENT ARTICLE WITH IMPROVED BODY FIT

CROSS REFERENCE TO RELATED APPLICATIONS

This application claims the benefit of U.S. Provisional Application No. 60/702,437 filed on Jul. 26, 2005 and U.S. Provisional Application No. 60/812,767 filed on Jun. 12, 2006.

FIELD OF THE INVENTION

The present invention concerns an absorbent article, preferably a disposable absorbent article, such as a diaper. The present invention specifically relates to an absorbent core for such an absorbent article that provides the article with improved softness and conformity to a wearer's body. This absorbent core is also useful for providing an absorbent article having increased wearing comfort.

BACKGROUND OF THE INVENTION

Absorbent articles, such as diapers and adult incontinence products, are well known articles of commerce. Multiple attempts have been made to provide them with an overall good fit and with a high absorbent capacity. Modern diapers make use of superabsorbent materials which allow for storage of significant amounts of aqueous liquids such as urine (e.g., on the order 300 ml for a typical baby diaper).

While such an absorbent article is generally a disposable product, it is frequently worn over many hours and worn in a dry state as well as in a urine loaded state. As a result, providing good wearing comfort is very important both when the article is dry and when the article is fully or partially loaded with urine (or other bodily liquids).

One way the art has approached wearing comfort is to provide thinner absorbent articles. For example, U.S. Pat. No. 4,673,402 describes an absorbent article with a dual layer core where the lower core component has a relatively high concentration of superabsorbent material and a relatively high density. U.S. Pat. No. 4,950,264 describes sanitary napkins with fiber/superabsorbent material blends where the superabsorbent is at a relatively high concentration. U.S. Pat. No. 5,102,597 describes absorbent polymeric macrostructures that comprise an interparticle crosslinked aggregate where individual superabsorbent particles are reacted with an interparticle crosslinking agent to form an aggregate which may take a sheet form. U.S. Pat. No. 5,411,497 discloses an absorbent article which includes superabsorbent material located in discrete pockets formed between a first and a second carrier layer and water-sensitive attaching means for securing the carrier layers together to form the pockets. U.S. patent application Ser. No. 10/776,839 discusses absorbent articles with a discontinuous layer of superabsorbent material. The layer may contain up to 20% of an absorbent fibrous material.

The art has also considered increasing density as a means to achieve thinness. For example, U.S. Pat. Application Publication 2005/0119632 discloses absorbent structures said to feature a relatively high concentration of superabsorbent material, a relatively high density and a relatively high level of flexibility.

However, there is a continuing need for absorbent articles having improved thinness and flexibility that maintain the capability to acquire and store enough of the fluid deposited thereon so as to continue to provide desirable wearer skin dryness and satisfactory leakage performance. Caregivers and adult wearers of such absorbent articles desire improved discretion in order that a diaper is less visible under clothes or, in the case of an infant diaper, looks more like underwear. More conformable cores are also desired in order to reduce the amount of material placed between a wearer's legs.

SUMMARY OF THE INVENTION

The present invention is directed to an absorbent article, preferably a disposable absorbent article, such as a diaper. The diaper has a thin, conformable absorbent core where the core structure provides the diaper with improved flexibility as measured using a circular bend test. Suitably, the diaper has a core region with a circular bend flexibility of less than about 15 N and an acquisition rate on the third gush of less than about 170 seconds and/or less than about 190 seconds.

Said core of the articles herein comprises:
i) a storage system comprising at least one storage layer comprising at least one region, comprising superabsorbent material and having a basis capacity of more than 10 $l/m^2$ and an absorption efficiency of at least 6.5 $ml/cm^3$;
ii) a substantially cellulose-free acquisition system comprising an acquisition/storage layer comprising at least one region, comprising superabsorbent material and having a basis capacity of from 1.5 to 10 $l/m^2$ and an absorption efficiency of from 2 to 14 $ml/cm^3$.

DETAILED DESCRIPTION

The present invention is directed to an absorbent article, preferably a disposable absorbent article, such as an infant diaper or adult incontinence product.

As used herein, the following terms have the following meanings:

The terms "superabsorbent material"; "superabsorbent polymer"; "SAP"; "absorbent gelling material" and "AGM" all refer to a polymeric material that is capable of absorbing at least about 5 times its weight of an aqueous fluid such as 0.9% saline as measured using the Centrifuge Retention Capacity test as is known to those of skill in the art.

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinence briefs, training pants, diaper holders and liners, sanitary napkins and the like.

"Diaper" refers to an absorbent article generally worn by infants and incontinent persons about the lower torso.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

The terms "comprise," "comprising," and "comprises" specify the presence of what follows (e.g., a component) but do not preclude the presence of other features, elements, steps or components known to the art or disclosed herein.

A structure (e.g., layer) that is "substantially cellulose free" means that the structure comprises less than 10% (by weight of the structure) cellulose fibres, typically less than 5% cellulose fibres or less than 1% cellulose fibres, or optionally no cellulose fibres, and typically it means that the structure comprises at least about 90% superabsorbent material. Preferably, such substantially cellulose free structures comprise at least about 95% superabsorbent material, or in certain embodiments at least about 99% superabsorbent material.

All percentages, ratios and proportions used herein are by weight unless otherwise specified.

Figure 1:
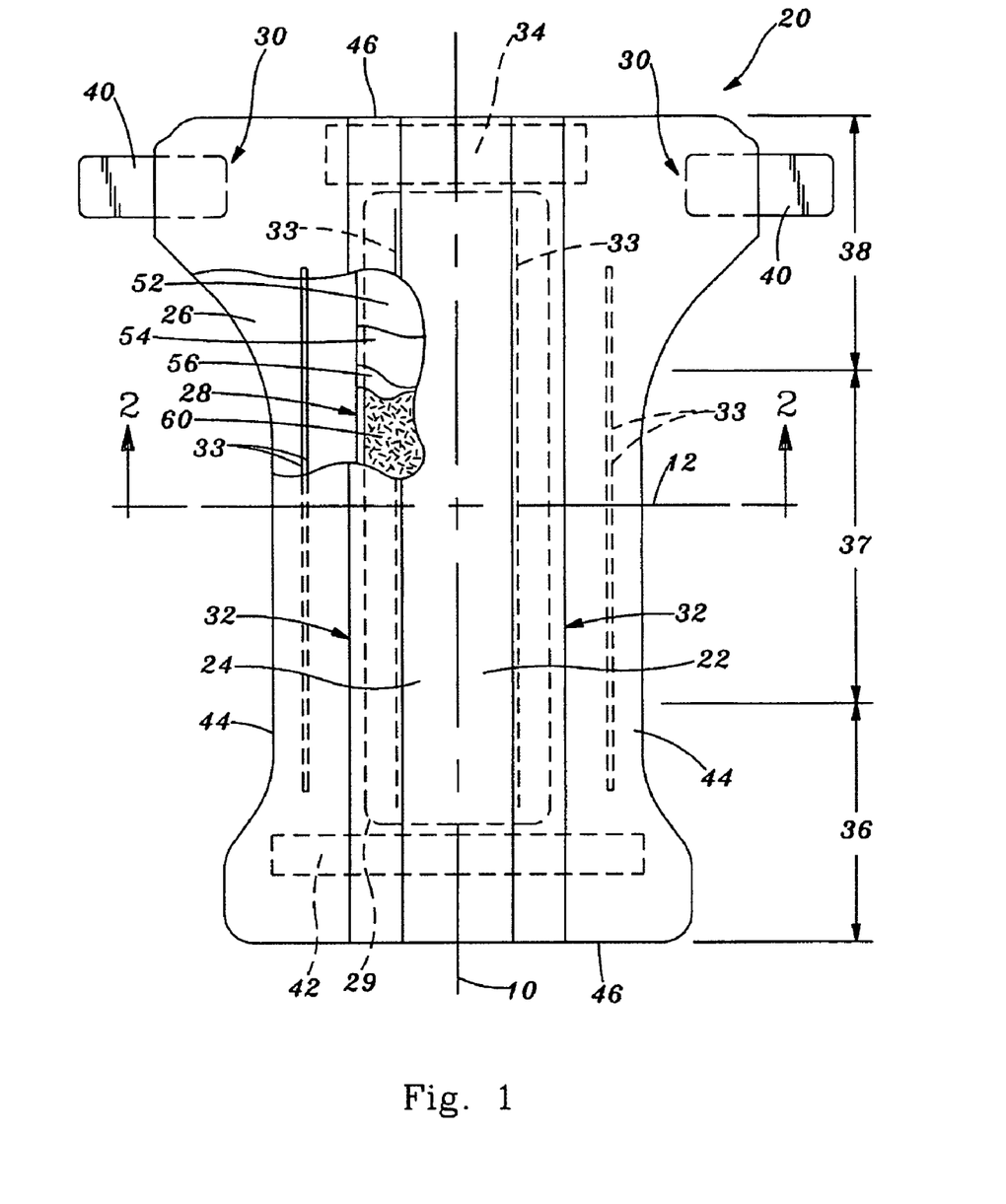
FIG. 1 is a plan view of a diaper as a preferred embodiment of an absorbent article according to the present invention.

FIG. 1 is a plan view of a preferred embodiment of an absorbent article according to the present invention diaper 20. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20 and does not include core 28 thereof. The chassis 22 comprises an outer covering including a liquid pervious topsheet 24 and backsheet 26. The chassis preferably further includes side panels 30, elasticized leg cuffs 32, and elastic waist feature 34, the leg cuffs 32 and the elastic waist feature each typically comprise elastic members 33. One end portion of the diaper 20 is configured as a first waist region 36 of the diaper 20. The opposite end portion is configured as a second waist region 38 of the diaper 20. An intermediate portion of the diaper 20 is configured as a crotch region 37, which extends longitudinally between the first and second waist regions 36 and 38. The waist regions 36 and 38 may include elastic elements such that they gather about the waist of the wearer to provide improved fit and containment (e.g., elastic waist feature 34). The crotch region 37 is that portion of the diaper 20 which, when the diaper 20 is worn, is generally positioned between the wearer's legs. The diaper 20 is depicted with its longitudinal axis 10 and its transverse axis 12. The periphery of the diaper 20 is defined by the outer edges of the diaper 20 in which the longitudinal edges 44 run generally parallel to the longitudinal axis 10 of the diaper 20 and the end edges 46 run between the longitudinal edges 44 generally parallel to the transverse axis 12 of the diaper 20. The chassis also comprises a fastening system, which may include at least one fastening member 40 and at least one landing zone 42.

For unitary absorbent articles, the chassis 22 comprises the main structure of the diaper with other features added to form the composite diaper structure. While diaper 20 may be assembled in a variety of well-known configurations, preferred diaper configurations are described generally in U.S. Pat. Nos. 4,940,464, 5,554,145; 5,569,234; 6,004,306, U.S. patent application Ser. No. 10/171,249 and in U.S. patent application Ser. No. 10/824,121.

The absorbent core 28 in FIG. 1 generally is disposed between the topsheet 24 and the backsheet 26. The absorbent core 28 may comprise any absorbent material that is generally compressible, conformable, non-irritating to the wearer's skin, and capable of absorbing and retaining liquids such as urine and other certain body exudates. Exemplary absorbent structures for use as the absorbent assemblies are described in U.S. Pat. Nos. 4,610,678; 4,834,735; 5,260,345; 5,387,207; 5,397,316; and 5,625,222.

Figure 2:
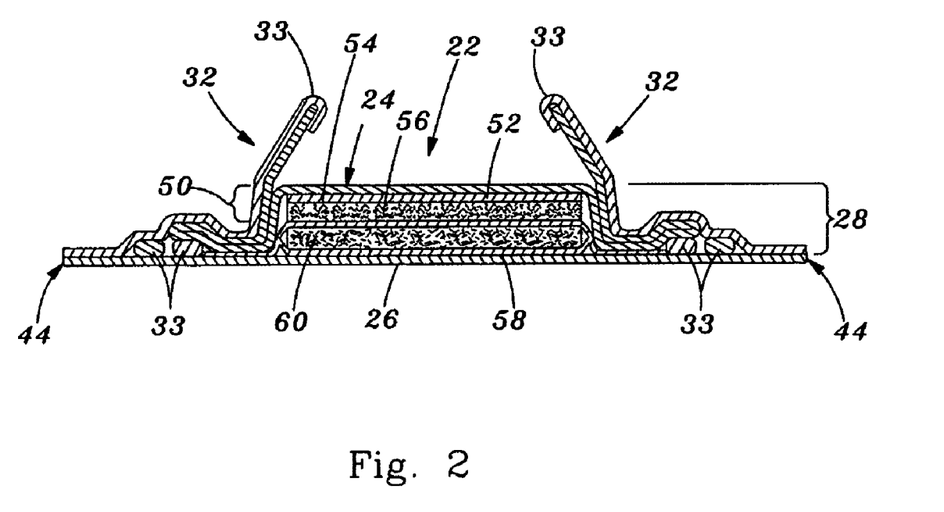
FIG. 2 is a cross-sectional view of the diaper shown in FIG. 1 taken along the sectional line 2-2 of FIG. 1.

As can be seen more clearly in FIG. 2, absorbent core 28 may comprise at least two layers: acquisition system 50 which comprises at least acquisition/storage layer 54 that provides acquisition along with temporary distribution and storage of acquired fluids and permanent storage of a portion thereof and storage system 60 which provides the majority of the storage capacity of diaper 20.

The topsheet 24 is compliant, soft feeling, and non-irritating to the wearer's skin. Further, the topsheet 24 is liquid pervious permitting liquids to readily penetrate through its thickness. A suitable topsheet 24 can be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. In one embodiment, the topsheet 24 is made of a hydrophobic material to isolate the wearer's skin from liquids in the absorbent core 10. Preferably the topsheet comprises a means to adjust hydrophilicity of the material.

A preferred topsheet 24 comprises a nonwoven material made using means well known to those skilled in the fabrics art. Preferably, the topsheet 24 has a basis weight from about 10 to about 25 g/m$^2$, a minimum dry tensile strength of at least about 150 g/cm in the machine direction and a strikethrough of less than about 3 seconds according to European Disposables and Nonwovens Association standard method 150.4-99. One suitable topsheet 24 comprises a polypropylene spunbonded nonwoven comprises fibers of less than 3 denier having a basis weight of about 18 g/m$^2$ as is available from BBA Fiberweb of Simpsonville, S.C.

The backsheet 26 is preferably joined to the topsheet 24 at least about a portion of the periphery thereof. The backsheet 26 prevents exudates absorbed by the absorbent core 28 and contained within diaper 20 from soiling other external articles that may contact the diaper 20, such as bed sheets and clothing. The backsheet 26 is preferably manufactured from a thin polymer film. In one preferred embodiment the film comprising backsheet 26 is impervious to liquids. Typically, the backsheet 26 comprises a layer of polyethylene film having a basis weight between about 10 g/m$^2$ and about 30 g/m$^2$, although other flexible, liquid impervious materials can be used. Preferably, the film is breathable (e.g., via micropores) so as to permit vapors to escape from the diaper 20 while still preventing exudates from passing through the backsheet 26. Particularly preferred backsheet materials have a nonwoven laminated to the film layer so as to make backsheet 26 more "cloth-like". Such a nonwoven layer may comprise a nonwoven material (e.g., one having a spunbonded or other suitable structure) with a basis weight between about 15 g/m$^2$ and about 25 g/m$^2$. Suitable materials for use as backsheet 26 are available form Clopay Plastic Products Company of Mason, Ohio.

The diaper 20 may also include such other features (not shown) as are known in the art including front and rear ear panels, waist cap features, elastics and the like to provide better fit, containment and aesthetic characteristics. Such additional features are well known in the art and are, e.g., described in U.S. Pat. No. 3,860,003 and U.S. Pat. No. 5,151, 092.

In order to keep the diaper 20 in place about the wearer, at least a portion of the first waist region 36 is attached by the fastening member 42 to at least a portion of the second waist region 38, so as to form leg opening(s) and a waist opening. The fastening system is designed to allow an article user to hold one element of the fastening system such as the fastening member 42, and connect the first waist region 36 to the second waist region 38 in at least two places. This is achieved through manipulation of bond strengths between the fastening device elements.

FIG. 2 shows a cross section of FIG. 1 taken along section line 2-2 of FIG. 1. Starting from the body facing side, the diaper comprises the topsheet 24, the components of the absorbent core 28, and the backsheet 26. Absorbent core 28 preferably comprises an acquisition system 50, which preferably comprises an acquisition layer 52 underlying topsheet 24 and acquisition/storage layer 54 disposed between acquisition layer 52 and the remaining component of core 28, storage system 60.

In particularly preferred embodiments, core 28 is narrower in crotch region 37 than it is in either of waist regions 36, 38. Preferably, the ratio of the width of core 28 at transverse axis 12 to the widest lateral width thereof in either of first waist region 36 or second waist region 38 is less than 1.0. More preferably the ratio is less than about 0.8, most preferably less than about 0.7.

In one preferred embodiment acquisition layer 52 comprises a non-woven. Alternatively acquisition layer 52 may comprise a chemically stiffened, twisted and curled fibers, foams or other materials suitable for acquiring aqueous fluids as are known to the art. As will be discussed in below, acquisition/storage layer 54 is substantially free of cellulosic fibers and comprises a highly permeable superabsorbent material.

Preferably, acquisition/storage layer 54 is in direct contact with storage system 60. Alternatively, storage system 60 may be wrapped by a core wrap material so as to dispose a layer between storage system 60 and acquisition/storage layer 54. In one preferred embodiment the core wrap material comprises an upper wrap layer 56 and a lower wrap layer 58. No matter what the relationship between acquisition/storage layer 54, storage system 60 and various arrangements of wrap materials, acquisition/storage layer 54 and storage system 60 must be in fluid communication. The material comprising wrap layers 56, 58 preferably is a nonwoven material. One preferred material comprises a spunbonded, a melt-blown and a further spunbonded layer (i.e., a SMS material). The non-woven materials are suitably made using synthetic fibers, such as polyethylene, polyester and, most preferably, polypropylene. Highly preferred are permanently hydrophilic non-wovens, and in particular nonwovens with durably hydrophilic coatings. Such hydrophilicity may be provided by surfactant treatment of the nonwoven. An alternative material comprises an SMMS-structure or a cellulosic tissue structure.

Similarly, but not shown, acquisition/storage layer 54 may be provided with a wrap material so as to enclose the layer. Materials suitable for upper and lower wrap layers 56, 58 are also suitable for use as a wrap material in designs for core 28 where it is desired to wrap acquisition/storage layer 54.

In a third alternative, wrap materials 56, 58 enclose both acquisition/storage layer 54 and storage system 60. In this embodiment acquisition/storage layer 54 and storage system 60 are in direct facing contact.

Suitably, acquisition/storage layer 54 has the same area as storage system 60 or smaller. Preferably, acquisition/storage layer 54 is laterally centered on storage system 60 with the same lateral width but a shorter longitudinal length than storage system 60. Acquisition/storage layer 54 may also be narrower than storage system 60 while remaining centered thereon. Said another way, acquisition/storage layer 54 suitably has an area ratio with respect to storage system 60 of 1.0. Preferably, the area ratio is less than 1.0 (e.g., less than about 0.75), more preferably less than about 0.50.

When the acquisition/storage layer 54 is longitudinally shorter than the storage system 60, it is positioned such that more than 50% of its longitudinal length is forward of transverse axis 12. This positioning is desirable so as to place acquisition/storage layer under the point where urine is most likely to first contact diaper 20 (Sometimes called the "pee point"). Such positioning will facilitate acquisition of liquids absorbed by acquisition/storage layer 54.

Also, both acquisition/storage layer 54 and storage system 60 may comprise an uneven distribution of superabsorbent material basis weight in one or both of the machine and cross directions. Such uneven basis weight distribution may be advantageously applied in order to provide extra, predetermined, localized absorbent capacity to diaper 20. For example, the basis weight of superabsorbent material in one or both of acquisition/storage layer 54 and storage system 60 could be increased in the region of core 28 adjacent the "pee point". This "profiled" distribution can also be used to provide diaper 20 with a desirable configuration to core 28 for improved body fit. For example, predetermined regions of low superabsorbent basis weight could be provided to create preferential fold zones in the core to help insure that core 28 flexes in a predetermined manner.

In alternative embodiments (not shown), the article may be preformed by the manufacturer by joining opposing portions of the longitudinal edges 44 that lie adjacent to the end edges 46 to create a pant. The term "pant", as used herein, refers to disposable garments having a waist opening and leg openings designed for infant or adult wearers. A pant may be placed in position on the wearer by inserting the wearer's legs into the leg openings and sliding the pant into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the term "pant" is used herein, pants are also commonly referred to as "closed diapers", "prefastened diapers", "pull-on diapers", "training pants" and "diaper-pants". Suitable pants are disclosed in U.S. Pat. Nos. 5,246,433; 5,569,234; 6,120,487; 6,120,489; 4,940,464; 5,092,861; 5,897,545; 5,957,908 and in U.S. Pat. Application Publication 2003/0233082A1.

In additional alternative embodiments (also not shown) acquisition/storage layer 54 and storage system 60 can comprise a removable/replaceable component of an absorbent article. Such removable/replaceable components allow the absorbent article to be "refreshed" without the necessity of changing the entire article. The acquisition/storage layer 54 and storage system 60 are disposed beneath at least one fluid permeable layer similar to topsheet 24. Such embodiments having removable/replaceable components are described more fully in one or more of the following: U.S. patent application Ser. No. 08/828,005, filed in the name of Lavon, et al. on Mar. 27, 1997 and Ser. No. 11/099,791 filed in the name of Lavon, et al. on Apr. 4, 2005 and in U.S. Pat. Publications 2004/0039361, 2002/0091368, 2003/0199844, 2004/0024379, 2004/0030314.

The storage system 60 herein has at least one storage layer with at least one region with superabsorbent material. This region is at least 20 mm×15 mm (length×width or width× length). Typically, the absorbent layer has a multitude of such regions, or consists of such regions.

The region(s) of the storage layer herein have a basis capacity of more than 10 l/m$^2$ and an absorption efficiency of at least 6.5 ml/cm$^3$, as determined by the method described herein.

Preferably, the region(s) of the storage layer have a basis capacity of at least 12 l/m$^2$, more preferably at least 15 l/m$^2$;

and it may be useful that the basis capacity is less than 36 l/m2; in one embodiment, the basis capacity is from 15 and 25 l/m².

Preferably, the region(s) of the storage layer have an absorption efficiency of at least 10 ml/cm³ and in one embodiment the absorption efficiency is from 10 ml/cm³ to 25 ml/cm³, or from 12 ml/cm³ to 20 ml/cm³ or from 15 ml/cm³ to 20 ml/cm³.

It may be preferred that the storage layer as a whole has a basis capacity and absorption efficiency within the ranges described herein above, and/or that the storage layer has an average basis capacity and an average absorption efficiency within the ranges specified above.

In one embodiment, the (thin) storage system 60 is obtained by stabilising the super absorbent material with a fibrous layer of thermoplastic (adhesive) material, e.g., which allows removal of some or all of the (absorbent) cellulose fibres that are often present in the storage core to stabilise the superabsorbent material. The resulting storage system (60), storage layer and region(s) thereof, may be substantially cellulose (fibres) free, e.g., comprises as absorbent component only superabsorbent material as described herein, as is for example also described in aforementioned U.S. patent application Ser. No. 10/776,839. The storage system 60 or layer or region(s) thereof may thus comprises a superabsorbent material that is stabilized by a fibrous layer of thermoplastic material, preferably a thermoplastic adhesive to provide dry and wet immobilization of the superabsorbent material. The storage system 60 is then substantially free of cellulosic fibers.

A particularly preferred superabsorbent material has an Absorption Against Pressure (AAP) of at least about 20 g/g. Preferably, AAP is greater than about 23 g/g, more preferably greater than about 25 g/g. AAP is measured according to the method described in the TEST METHODS section below.

The superabsorbent materials of the storage system 60 may be used at an average basis weight of at least about 200 g/m², or at least at 300 g/m². The storage system 60 according may have an average density greater than about 0.3 g/cm³, or 0.4 g/cm³ or greater, 0.45 g/cm³ or greater The super absorbent material of the storage system 60 may typically have a saline flow conductivity (SFC) of at least $40 \times 10^7$ cm³ s/g; or preferably $80 \times 10^7$ cm³ s/g or more; or possibly $100 \times 10^{-7}$ cm³ s/g or more; or even a SFC of $120 \times 10^7$ cm³ sec/g or more. This SFC is a measure of permeability and an indication of porosity is provided by the saline flow conductivity of the gel bed as described in U.S. Pat. No. 5,562,646, (Goldman et al.) issued Oct. 8, 1996 (whereby however a 0.9% NaCl solution is used instead of Jayco solution).

Acquisition/storage layer 54 of the acquisition system 50 cooperates with storage system 60 to make more efficient use of the capacity thereof by providing temporary capillary storage of acquired fluids to allow time for fluid distribution into storage system 60. In addition, because acquisition/storage layer 54 comprises a superabsorbent material, it provides at least a portion of the ultimate storage capacity of absorbent core 28.

Importantly, because acquisition/storage layer 54 is intended to provide at least some temporary capillary storage and distribution of acquired fluid, it has a more open structure when wet than storage system 60 (i.e., the wet porosity is greater). The art has typically used fibrous structures (e.g., blends of cellulose fluff and superabsorbent material or crosslinked cellulose fibers for this purpose). However, such fibrous structures have considerable dry bulk compared to the substantially cellulosic fiber free acquisition/storage layers 54 of the present invention. Suitable superabsorbent materials for use in acquisition/storage layer 54 are described in U.S. patent application Ser. No. 10/950,011, in U.S. patent application Ser. No. 10/941,672, U.S. patent application Ser. No. 11/091,255 and in JP 2004-105118, entitled "An Aqueous-Liquid-Absorbing Agent and Its Production Process", filed in the name of Nippon Shokubai Co. Ltd. On Mar. 31, 2004. The superabsorbent material may be used at a basis weight of at least about 100 g/m², preferably at least about 150 g/m², more preferably at least about 200 g/m², to produce acquisition/storage layer 54.

The acquisition system 50 comprises an acquisition/storage layer 54 that comprises at least one region with superabsorbent material, and having a basis capacity of from 1.5 to 10 l/m² and an absorption efficiency of from 2 to 14 ml/cm³. Such a region is at least 40 mm×20 mm (length×width or width×length). The acquisition/storage layer 54 may comprise a multitude of such regions or it may consist of such regions.

Preferably, the region(s) of the acquisition/storage layer 54 have a basis capacity of from 1.5 to 6 l/m², more preferably from 1.8 to 5 l/m² and in one embodiment from 2 to 4 l/m². Preferably, the region(s) of the acquisition/storage layer 54 have an absorption efficiency of from 3 to 12 ml/cm³; or more preferably from 4 to 9 ml/cm³.

It may be preferred that the acquisition/storage layer 54 as a whole has a basis capacity and absorption efficiency within the ranges described herein above, and/or that the acquisition/storage layer 54 has an average basis capacity and an average absorption efficiency within the ranges specified above.

In one embodiment, the acquisition/storage layer 54 comprises superabsorbent material that has a specific modified saline flow conductivity, herein referred to as modified SFC, of not less than $400 \times 10^{-7}$ cm³·s/g, more preferably not less than $500 \times 10^{-7}$ cm³·s/g, still more preferably not less than $700 \times 10^{-7}$ cm³·s/g, particularly preferably not less than $1,000 \times 10^{-7}$ cm³·s/g, as measured with the specific modified SFC test as set out in the above-mentioned U.S. patent application Ser. No. 11/091,255 and in JP 2004-105118. This modified SFC of this superabsorbent material of the acquisition system is preferably not more than $4,000 \times 10^{-7}$ cm³·s/g, more preferably not more than $3,000 \times 10^{-7}$ cm³·s/g.

Because an acquisition/storage layer 54 according to the present invention is substantially free of cellulosic fibers, it may have a higher density than components of an absorbent core used by the prior art for similar purposes. Suitably, an acquisition/storage layer 54 may have a density greater than about 0.3 g/cm³, or even greater than 0.4 g/cm³.

Acquisition/storage layer 54 and storage system 60 also cooperate to provide diaper 20 with improved wearer fit and comfort. Specifically a diaper 20 that comprises a core 28 where the acquisition system 50 includes at least an acquisition/storage layer 54 according to the present invention has desirable low caliper and crotch flexibility. As will be recognized, a low caliper and a flexible material result in a flexible core that can more closely conform to a wearer's body throughout the full range of wearer motion. Such thin/flexible diapers are also less visible under a wearer's clothing and can have a very underwear-like appearance.

As noted above, cores 28 according to the present invention have a desirable low caliper. Desirably, the acquisition system 50 of the present invention comprises both an acquisition layer 52 and an acquisition/storage layer 54. For a core 28 of this construction dry core caliper is less than about 5 mm when measured at the center of acquisition layer 52. Preferably, the caliper of core 28 is less than about 4.5 mm, more preferably less than about 4 mm when measured at the center of acquisition layer 52. Structures that do not incorporate the acquisition layer 52 are even thinner.

It should be noted that, when many of the absorbent structures of the art discuss caliper, the caliper of the absorbent structure is discussed in terms of only a single layer, rather than the assembled layers necessary to form a complete core 28 for a diaper 20. Thus it is believed the low caliper of a core 28 of the present invention is particularly advantageous. Said another way, the low caliper of core 28 provides diaper 20 with a desirable low caliper. That is, the thickness of all diaper components between the body surface of the topsheet and the garment surface of the backsheet is meaningfully less than the thickness of prior art diapers. For example, in one embodiment, a diaper 20 that comprises a core 28 according to the present invention has a dry caliper (measured 10 cm from the front edge 29 of core 28) that is less than about 5 mm. Preferably, the dry caliper of diaper 20 is less than about 4.5 mm, more preferably less than about 4 mm.

Core 28 according to the present invention is also desirably flexible so as to facilitate reduced bulk and improved conformity of diaper 20. Without being bound by theory, it is believed that the combination of a thin construction as discussed above (as is known, stiffness increases with thickness) and flexible joinder of the absorbent polymer particles by the thermoplastic material (see, for example, published U.S. Pat Application 2004/0162536) cooperate to provide the desirable flexibility. As a result, core 28 can more readily conform to varying wearer body shapes and respond to wearer motion. As can be seen in Example 1, diaper products of the prior art vary widely in flexibility (from 4.0 N to 70.5 N when evaluated according to the Circular Bend Flexibility test). It will be recognized that such flexibility is a result of many factors coming together in a finished diaper product. For example the Circular Bend Flexibility of Comparative Diapers A and B is markedly different although the diapers have very similar storage systems. Without being bound by theory, it is believed that the difference in Circular Bend Flexibility can be attributed to the difference in the acquisition systems. Specifically, the dual layer acquisition system used in Comparative Diaper A has desirable fluid handling properties (e.g., the dual layer acquisition system provides substantial temporary storage for urine "gushes" with resulting rapid acquisition). These benefits come at the price of substantially less flexibility than Comparative Diaper B. Reference to Example 2 shows that the core designs of the present invention maintain much of the improved flexibility of Comparative Core B (~12N for a core according to the present invention vs. ~44N for Comparative Core A) while also providing the desirable fluid handling properties of Comparative Core A (third gush acquisition rate of ~100 seconds for a core according to the present invention vs. ~200 seconds for Comparative Core B). Specifically, replacing the dual layer acquisition system of Comparative Diaper A with a storage/distribution system according to the present invention provides much of the rapid acquisition of the dual layer system while remaining thin and flexible when dry so as to provide much of the dry flexibility of Comparative Diaper B.

Suitably an absorbent core 28 according to the present invention has a Circular Bend flexibility of less than about 13 N, preferably less than about 12 N, and more preferably less than about 10 N. Similarly, an absorbent article according to the present invention has a Circular Bend Flexibility substantially lower than that of commercially available and prior art diapers. Suitably, an absorbent article according to the present invention has a Circular Bend Flexibility less than about 15 N in a specimen taken from crotch region 37, forward of the lateral centerline of absorbent core 28 thereof. Preferably, the Circular Bend Flexibility in crotch region 37 is less than about 13.5 N, more preferably less than about 11 N. A method for measuring Circular Bend Flexibility is given in the Test Methods section below.

The absorbent cores 28 of the present invention not only have the low caliper and improved flexibility discussed above they also provide a wearer with desirable fluid handling properties. With respect to absorbent articles at least two types of fluid handling properties need to be considered: fluid acquisition and fluid storage capacity (e.g., reflected by the SFC of the acquisition layer's and storage system's superabsorbent material and/or its acquisition rates, as described herein).

An absorbent article should have good fluid acquisition properties in order to rapidly transfer aqueous fluids from the body surface of the absorbent article to minimize free fluid that can bypass cuffs and waistbands with a resulting leak. In the case of the present invention, acquisition/storage layer 54 cooperates with acquisition layer 52 (when such an acquisition layer is present) to provide void volume for containing "gushes" of aqueous liquids so as to allow time for storage system 60 to acquire and permanently store such fluids. Because acquisition/storage layer 54 comprises a highly permeable superabsorbent material, such void volume is maintained even after the superabsorbent material comprising acquisition/storage layer 54 begins to swell after exposure to an aqueous fluid. Fluid acquisition properties can be conveniently measured using the Fluid Acquisition test described in the TEST METHODS section below. This test measures the time required for an absorbent article to acquire a predefined volume of fluid that is delivered in a series of "gushes". The volume and delivery rate are intended to represent typical conditions for a specific size absorbent article. Depending on the size of the article, the time required to acquire the third or fourth gush of fluid can be an important measure of acquisition performance. Suitably, an absorbent article according to the present invention has a third gush acquisition rate of less than about 170 seconds, preferably less than about 150 seconds, more preferably less than about 130 seconds. Particularly preferred embodiments have a third gush acquisition rate of less than about 100 seconds. For larger sizes, acquisition rate for a fourth gush is also important. Suitably, an absorbent article according to the present invention has a fourth gush acquisition rate of less than about 190 seconds, preferably less than about 180 seconds, more preferably less than about 170 seconds.

Specifically, a core 28 of the present invention must provide sufficient storage capacity to function while simultaneously providing substantially reduced dry caliper and improved flexibility. As is also known, the required absorbent capacity for an absorbent article is basically defined by the intended use thereof. That is, an absorbent article intended for adult incontinence uses will have a larger design capacity than and absorbent article intended for an infant. Importantly, an absorbent core 28 according to the present invention does not give up the capacity to store an appropriate quantity of aqueous fluid in order to provide a reduction in core caliper. One way of considering capacity is as normalized capacity, that is capacity per unit area. This approach takes into account that absorbent articles designed for larger wearers will have both a larger design capacity and a larger core area to absorb fluids deposited thereon. A method for normalized capacity is given in U.S. patent application Ser. No. 11/091,255. Suitably, a core 28 according to the present invention will have a normalized capacity in the portion thereof that comprises acquisition storage layer 54 of greater than about 0.3 g/cm$^2$. Preferably, the normalized capacity in the portion thereof that comprises acquisition storage layer 54 is greater than about 1.0 g/cm$^2$, more preferably greater than about 2.0 g/cm$^2$. In those portions of core 28 that do not comprise acquisition/ storage layer 54 the normalized capacity may be lower. For designs where the bulk of the capacity for aqueous liquids is within or adjacent to the crotch region 37, suitably, the normalized capacity in such areas is less than about 0.9 g/cm$^2$, preferably less than about 0.5 g/cm$^2$, more preferably less than about 0.2 g/cm$^2$.

In an alternative embodiment core 28 is designed to provide a substantial portion of the ultimate storage in one or both of waist regions 36, 38. For this embodiment the normalized core capacity in one or both of waist regions 36, 38 may be equal to or higher than the normalized core capacity in crotch region 37. For example such waist region normalized core capacity may be greater than about 1.0 g/cm$^2$, even greater than about 2.0 g/cm$^2$. For this embodiment, the area of crotch region 37 is less than the area of the embodiment discussed above where the bulk of the capacity for aqueous liquids is within or adjacent to the crotch region 37 and acquisition/storage layer 54 may extend into waist regions 36, 38.

As will be recognized, if it is desired to calculate the total capacity of a core 28, the respective areas of a core 28 with and without acquisition layer 54 can be determined using means known to the art (e.g., image analysis) and those areas multiplied by the normalized capacity for the area to determine the total capacity of a core 28 having a particular size.

Storage system 60 can suitably be produced using the method described in the aforementioned U.S. patent application Ser. No. 10/776,839.

Acquisition/storage layer 54 can be produced using a method that is substantially the same as that used to produce storage system 60. The main difference is that, rather than being provided with an uneven surface so as to provide areas of junction where an adhesive directly contacts a substrate layer as described in U.S. patent application Ser. No. 10/776, 839, a laydown drum is provided with a series of "pockets" having a shape and volume substantially defined by the desired shape and volume of acquisition/storage layer 54. As will be recognized, the shape and volume of these pockets may be used to provide a predefined superabsorbent material profile to one or both of acquisition/storage layer 54 and storage system 60. This laydown drum is provided with vacuum means as described in the aforementioned U.S. patent application Ser. No. 10/776,839 that is suitable for drawing a substrate into the pocket. Any nonwoven suitable for use as a substrate for storage system 60 is also suitable for use to produce acquisition/storage layer 54.

In one preferred embodiment, storage system 60 and acquisition/storage layer 54 are produced so as to provide a core 28 with no upper wrap layer 56 therebetween. One suitable process for producing this structure is shown in FIG. 3 and discussed in the following paragraphs.

Figure 3:
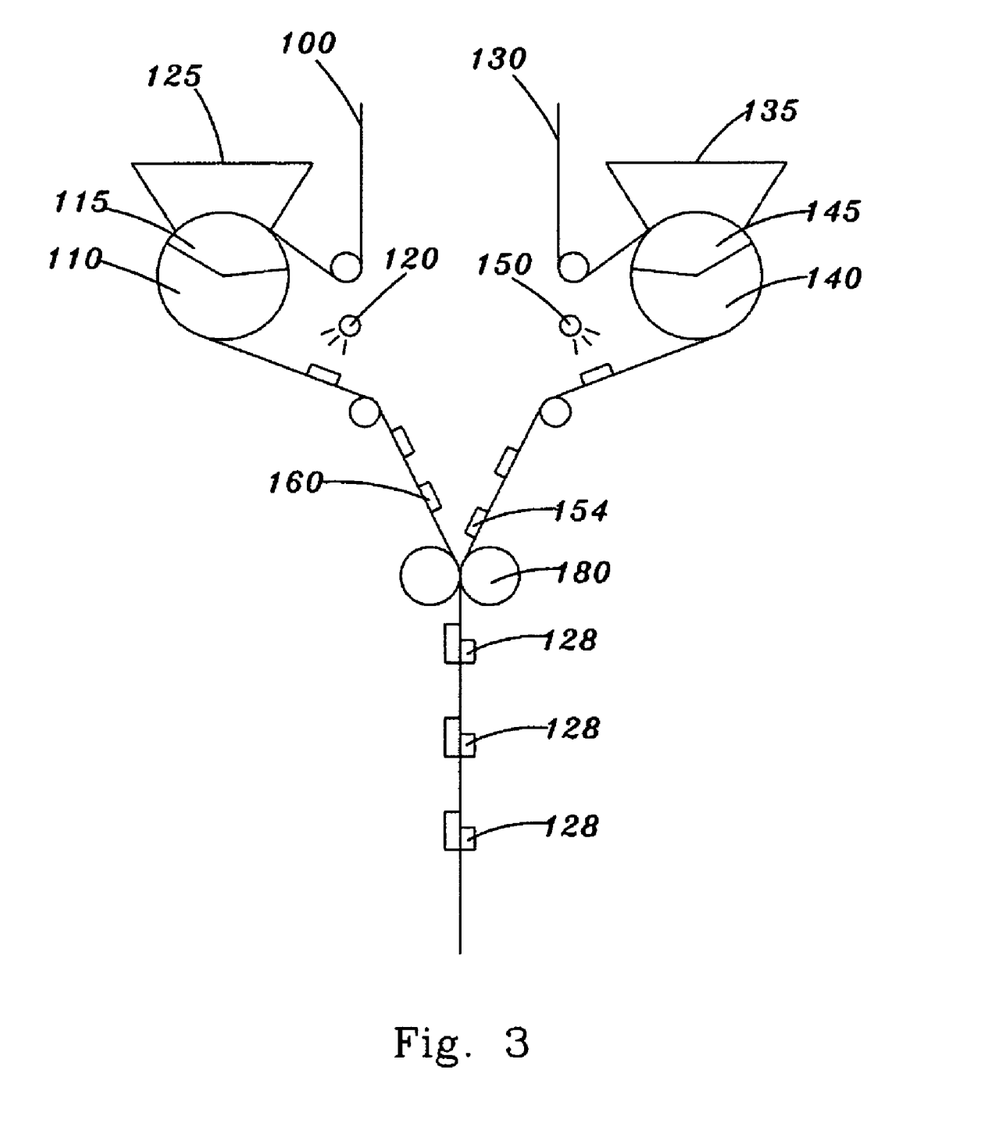
FIG. 3 is a schematic view of an apparatus for production of one preferred embodiment of the cores of the present invention.

As can be seen in FIG. 3, a storage layer precursor 160 can be produced by depositing a first superabsorbent material (not shown) that is contained in hopper 105 onto substrate 100. As described in U.S. patent application Ser. No. 10/776,839, first substrate 100 is caused to conform to depressions (not shown) in first laydown drum 110 by a vacuum in first vacuum portion 115 so as to enable filling the depressions with the first superabsorbent material as the depression passes under first hopper 105. After the depression passes under first hopper 105 the first superabsorbent material is stabilized with a thermoplastic polymer applied at first spray station 120 so as to form storage layer precursor 160.

Acquisition/storage layer precursor 154 can be produced in essentially the same manner. Second substrate 130 is caused to conform to a depression in second laydown drum 140 prior to filling with a second absorbent polymer (not shown) delivered from second hopper 135. The second superabsorbent material in the filled depressions is stabilized by thermoplastic polymer delivered from second spray station 150.

To form core precursors 128, the substrate webs carrying storage layer precursor 160 and acquisition/storage layer precursor 154 are phased for proper alignment using methods known to the art and combined at nip 180. As will be recognized, the rolls comprising nip 180 can be provided with pockets to receive precursors 160, 154 to enable the first and second substrates 100, 130 to be sealed about the periphery of storage layer precursor 160 effectively enclosing core precursor 128 in a wrap material. If necessary, one or both of the rolls comprising nip 180 could be heated to soften the thermoplastic material to facilitate the enclosure step.

As will also be recognized separate nips (not shown) essentially the same as nip 180 and a web of a suitable nonwoven material (not shown) could be provided between the spray stations 120, 150 and nip 180 if it was desired to enclose either or both of precursors 160, 154.

Test Methods

Fluid Acquisition

The fluid acquisition test provides a measure of the ability of an absorbent structure to rapidly acquire aqueous fluids under simulated use conditions. The sample is loaded with a gush of 0.9% saline solution at a predetermined volume and rate using a pump (The Model 7520-00 available from Cole Parmer Instruments Co. of Chicago, Ill. is suitable). The time to absorb saline solution is recorded by a timer. The gush is repeated at 5 minute gush intervals for 4 gushes. The detailed description below is directed to infant diapers, for other types of absorbent articles the gush volume and confining pressure may be adjusted as described herein.

The test sample, which comprises a core and includes a topsheet and a backsheet, is arranged to lie flat on a foam platform within a polymethyl methacrylate (e.g., PERSPEX) box (see the detail assembly of the test apparatus in U.S. Pat. No. 6,083,210) and a weight representative of a typical confining pressure is placed on a PERSPEX cover as discussed below. The following provides suitable setup parameters for various sizes of infant diapers. If a diaper product to be tested does not list a size, the product size is defined by determining the weight range with the greatest overlap with the weight ranges listed below.

| Size | Approx. Infant Wt (kg) | Loading Vol. (ml) | Loading Rate (ml/sec) | Confining Pressure Weight (kg) |
| --- | --- | --- | --- | --- |
| Newborn | <4 | 16 | 5.33 | 0.9 at each end of plate = 1.8 total |
| 1 | 4-6 | 24 | 8 | 2.3 at each end of plate = 4.6 total |
| 2 | 5-8 | 40 | 8 | 2.9 at each end of plate = 5.8 total |
| 3 | 7-13 | 50 | 10 | 4.5 at each end of plate = 9.0 total |
| 4 | 10-17 | 75 | 15 | 9.1 at each end of plate = 18.2 total |
| 5 and larger | >12 | 75 | 15 | 9.1 at each end of plate = 18.2 total |

If products with significantly different capacities from those listed in the table above are evaluated (such as can be envisaged for adult incontinence products or diapers for premature infants), the fluid volume per gush should be adjusted to 20% of the total article design capacity and the weight for the confining pressure should be adjusted to be representative of the pressure exerted a wearer on the product when the wearer is sitting. Design capacity can be determined by summing the capacity of superabsorbent material (defined as the Centrifuge Retention Capacity) and any contribution from fibrous material in the core (e.g., 4 g/g for cellulosic fibers). Any deviation from the standard test protocol should be recorded.

The outer surface of the backsheet faces the foam platform. A PERSPEX plate with a 5 cm diameter opening substantially in its middle is placed on top of the sample. The sample is oriented such that the topsheet is directly below the opening of the PERSPEX plate. The opening in the plate (i.e., the loading point for the saline solution) is placed about 10 cm from the front edge of the complete core and about in the halfway between the lateral sides of the core. Saline solution is introduced to the sample through the cylinder fitted and glued into the opening. Electrodes are about 1 mm to 2 mm above the surface of the absorbent structure and also connected to the timer. Loads are placed on top of the plate to simulate, for example a baby's weight. Two weights with an area of 744.6 $cm^2$ (51 cm×14.6 cm) appropriate for the particular size (see table above) are placed on top of the plate.

As saline solution is introduced into the cylinder, it builds up on top of the absorbent structure thereby completing an electrical circuit between the electrodes. This starts the timer. The timer is stopped and recorded when the absorbent structure has absorbed the gush, and the electrical contact between the electrodes is broken.

Acquisition rate is defined as the time in seconds required to absorb the gush volume that is delivered. The acquisition rate is calculated for each gush introduced into the sample.

Basis Weight

European Disposables and Nonwovens Association (EDANA) standard method for Mass per Unit Area (40.3-90) is suitable

Caliper

European Disposables and Nonwovens Association (EDANA) standard method for Thickness (No 30.5-99) is suitable. A suitable apparatus is described in paragraph 4.1. The specified pressure is 2.1 kPa.

Density

Divide the basis weight determined using the Basis Weight method by the caliper determined by the Caliper method.

Centrifuge Retention Capacity of Superabsorbent Material in the Region(s)

European Disposables and Nonwovens Association (EDANA) standard method 441.2-02 is suitable.

Centrifuge Retention Capacity (CRC) of Storage Layer or Acquisition/Storage Layer The CRC of region of the acquisition/storage layer or a region of the storage layer can be determined with a modified EDANA standard test method 441.2-02. Namely, this standard test is applied on a cut-out sample of a region of the storage layer or a region of the acquisition/storage layer (so the standard sample of 0.200 g of superabsorbent powder used in this test is now replaced by a cut-out sample of the region or regions of a layer). For the storage layer a sample size of 20 mm×15 mm is used. For the acquisition/storage layer a sample size of 40 mm×20 mm is used. The sample can be obtained by separating the absorbent core from the absorbent article, and then separating the distinctive layers of the absorbent core, to obtain the individual storage layer(s) and acquisition layer(s). This should be done such that a representative sample will be obtainable. The samples of the dimensions specified above can then be cut with a die-cutter of each layer. Each sample should then be handled and measured as specified in the EDANA method, e.g., stored in closed container and conditioned prior to measurement.

A CRC value per region (sample) will be obtained. If appropriate, a multitude of samples of a multitude of regions per layer may be cur out and measured and an average CRC per layer may be obtained.

Basis Capacity of a Region

The basis capacity of a region is calculated by multiplying the CRC of said region with the basis weight of said region, as may be determined per the methods above:

Basis capacity=$CRC$ of region*Basis Weight of region

Basis capacity is given in kg of fluid absorbed per m2 of layer. Since density of 0.9% saline solution is about 1 gram/cm3 it is typically reported in liter of fluid per m2 of layer, as also used herein.

An average basis capacity for a layer may also be obtained as set out above.

Absorption Efficiency of a Region

The absorption efficiency of a region is calculated by multiplying the CRC of the region with the density of said region, as may be determined per the methods set out above:

Absorption Effectiveness=$CRC$ of layer*density of the layer (It is reported in ml/cm3)

An average basis capacity for a layer may also be obtained as set out above.

Circular Bend Flexibility

Sample Preparation

This method is suitable for measuring the flexibility of absorbent articles or absorbent article components having a core with sufficient area to cut a 2.5 inch×6.5 inch (6.4 cm×6.4 cm) sample therefrom. Samples should equilibrate at 23° C.±2° C. and 50%±2% relative humidity for at least 2 hours before testing. Open the side seals if the absorbent article is a pants type diaper. Remove all elastics (leg cuffs, waist bands, etc.) from the absorbent article. Gently stretch the absorbent article on a flat surface, with the backsheet toward that surface, to eliminate any folds therein. Mark the intersection of the longitudinal and transverse axes of the absorbent core. Measure 62 mm along the longitudinal axis toward the front waist edge of the absorbent article, and make a second mark. Using a hydraulic press (suitable presses are available from Carver, Inc. of Wabash, Ind.) with a 2.5 inch square die (6.4 cm), cut a sample centered at the second mark.

Apparatus and Method

The circular bend method is performed on a constant rate of extension tensile tester with computer interface (a suitable instrument is the MTS Q-tester using Testworks 4 Software;

as is available from MTS Systems Corp, Eden Prairie, Minn.) and a 100 N load cell. The instrument is set up for a standard compression test using the platform and plunger fixtures described in ASTM D4032-94 (Standard Test Method for Stiffness of Fabric by the Circular Bend Procedure). The sample is centered on the platform over the aperture. The piston is rigidly connected to the crosshead of the tensile tester, centered on the aperture and positioned 20 mm above the top plane of the platform at the start of the test. Upon test initiation, crosshead motion causes the plunger to descend at a rate of 100 mm/min to a depth of 15 mm below the top plane of the platform.

Replicates and Calculations

At least 5 replicates for each sample are evaluated.

The circular bend flexibility is reported as the maximum peak force in Newtons (N). Each set of five identical replicates (or n replicates if n is greater than 5) is tested and the five values measured for that set are averaged as the value for the sample.

EXAMPLES

Example 1

This example is intended to show the flexibility of the core region of machine made diaper products of the prior art. In this example, commercially available diapers, and other diapers according to the prior art were evaluated for Circular Bend Flexibility in two sections of the crotch region (before and after the lateral centerline of the core) using the method described herein. The results of this evaluation can be found in Table 1.

TABLE 1

| Diaper Type | Circular Bend Flexibility Crotch Front (N) |
| --- | --- |
| Pampers Easy Ups ®[1] 3T/4T | 51.3 |
| Pampers Feel n Learn ®[1] | 24.4 |
| Huggies Pull Ups ®[2] Girl | |
| Size 2T/3T | |
| Size 3T/4T | 18.4 |
| Size 4T/5T | 24.7 |
| Huggies Pull Ups ®[2] Boy Size 4 | 15.6 |
| Pampers Cruisers ®[1] Size 4 | 49.3 |
| Huggies Supreme ®[2] Size 4 | 43.9 |
| Huggies Baby Shape ®[2] Size 4 | 70.5 |
| Comparative Diaper A[3] | 38.2 |
| Comparative Diaper B[4] | 50.1 |
| Cloth Underwear[5] | 4.0 |
| | 0.2 |

[1]Available from Procter & Gamble of Cincinnati, OH
[2]Available from Kimberly Clark of Neenah, WI
[3]Storage system according to published U.S. Pat Application 2004/0162536 with dual layer acquisition system comprising crosslinked cellulose fibers (250 g/m²) and carded/resin bonded polyester nonwoven (60 g/m²)
[4]Storage system according to published U.S. Pat Application 2004/0162536 with nonwoven acquisition layer comprising carded/resin bonded polyester nonwoven (43 g/m²)
[5]Hanes Her Way ® cotton briefs Size 4 available from Hanes Company, Inc. of Winston-Salem, NC, two plies of fabric in crotch area. A 10 N load cell was used in the force measurement instead of a 100 N load cell due to the high flexibility.

As can be seen, there is a wide variation in flexibility among the diapers tested and underwear is the most flexible of all products tested.

Example 2

This example is intended to compare the flexibility and acquisition rate of absorbent cores according to the present invention with two cores from the prior art. In this example the core samples are disposed on a backsheet comprising a laminate of a 18 g/m² spunbonded polypropylene from BBA Fiberweb of Simpsonville, S.C. and a 28 g/m² polyethylene film from Clopay Plastic Products Company of Mason, Ohio with a topsheet (18 g/m² spunbonded polypropylene from BBA Fiberweb of Simpsonville, S.C.) disposed thereon and are evaluated for Circular Bend Flexibility in the front portion of the crotch region (before the lateral centerline of the core) and Third Gush Acquisition Rate.

TABLE 2

Average Circular Bend

| Diaper Type | Flexibility Crotch Front (N) | Acquisition Rate 3rd Gush (seconds) |
| --- | --- | --- |
| Comparative Core A[1] | 44 | 90 |
| Comparative Core B[2] | 2 | 198 |
| Core According to Present Invention[3] | 12 | 97 |

[1]Storage system according to published U.S. Pat Application 2004/0162536 (800 g/m²) with dual layer acquisition system comprising crosslinked cellulose fibers (250 g/m²) and carded/resin bonded polyester nonwoven (60 g/m²)
[2]Storage system according to published U.S. Pat Application 2004/0162536 (400 g/m²) nonwoven acquisition layer comprising carded/resin bonded polyester nonwoven (43 g/m²)
[3]Storage system according to published U.S. Pat Application 2004/0162536 (680 g/m²), acquisition/storage layer according to the present invention (superabsorbent material according to U.S. Pat. Application Ser. No. 11/091,255 with a basis weight of 200 g/m²) and carded/resin bonded polyester nonwoven (60 g/m²)

Example 3

This example is intended to compare the dry caliper of diapers according to the present invention with commercially available diapers and a diaper made according to U.S. Pat Application Publication 2004/0162536. This comparison is shown in Table 3.

TABLE 3

| Product | Dry Caliper (mm) |
| --- | --- |
| Pampers ® Active Fit (size 4)[1] | 7.1 |
| Huggies ® Super-Flex (size 4)[2] | 7.2 |
| Huggies ®Pull-Ups ®Girl ®[3] | 3.2 |
| Huggies ®Pull-Ups ®Boy ®[3] | 4.0 |
| Diaper According to published U.S. Pat Application 2004/0162536[4] | 5.9 |
| Present Invention[5] | 3.9 |

[1]Available from Procter & Gamble GMBH of Schwalbach am Tanus, Germany
[2]Available from Kimberly Clark of Reigate, United Kingdom
[3]Available from Kimberly Clark of Neenah, WI
[4]Dual layer acquisition system: consists of curly cellulosic fiber (200 g/m²) and carded/resin bonded polyester nonwoven (60 g/m²)
[5]Acquisition/storage layer according to the present invention The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. As will be also be apparent to the skilled practitioner, all combinations of the embodiments and features taught in the foregoing disclosure are possible and can result in preferred executions of the invention. It is therefore intended to cover in the appended claims all such changes and modifications that are within the scope of this invention.

What is claimed is:

1. An absorbent article comprising:
   a) a fluid permeable topsheet;
   b) a backsheet, said backsheet being joined to said topsheet about a periphery of said absorbent article; and
   c) a core disposed between said topsheet and said backsheet, said core comprising:
      i) a storage system comprising at least one storage layer comprising at least one region, said storage system comprising less than 10% by weight of cellulose fibers and comprising at least 95% by weight of a superabsorbent material, said storage system region having a basis capacity of more than 10 $l/m^2$ and an absorption efficiency of at least 6.5 $ml/cm^3$;
      ii) an acquisition system comprising:
         a) an acquisition layer comprising a non-woven; and
         b) an acquisition/storage layer comprising at least one region, said acquisition/storage layer comprising less than 10% by weight of cellulose fibers and comprising at least 95% by weight of a superabsorbent material, said acquisition/storage region having a basis capacity of from 1.5 to 10 $l/m^2$ and an absorption efficiency of from 2 to 14 $ml/cm^3$;
   wherein said absorbent article has a circular bend flexibility of less than about 15 N in a crotch region thereof;
   wherein said superabsorbent material of said storage system is stabilized by a fibrous layer of thermoplastic adhesive.

2. An absorbent article as in claim 1 wherein said regions(s) of the storage layer has (have) a basis capacity of at least 15 $l/m^2$ and an absorption efficiency of at least 9 $ml/cm^3$.

3. An absorbent article as in claim 1 whereby said regions(s) of the acquisition/storage layer has (have) a basis capacity of from 1.8 $l/m^2$ to 4 $l/m^2$ and an absorption efficiency of from between 4 and 9 $ml/cm^3$.

4. An absorbent article as in claim 1 wherein, the absorbent article has an acquisition rate selected from measurements of at least one of the following gushes:
   a) on the third gush of less than about 170 seconds; or
   b) on the fourth gush of less than about 190 seconds.

5. An absorbent material as in claim 1 whereby said superabsorbent material in said acquisition/storage layer has a modified SFC of $400 \times 10^{-7}$ $cm^3 \cdot s/g$ or more, and said superabsorbent material in said storage layer has a SFC of $80 \times 10^{-7}$ $cm^3 \cdot s/g$ or more.

6. An absorbent article according to claim 1 wherein said absorbent article has a circular bend flexibility of less than about 11 N in a crotch region thereof.

7. An absorbent article according to claim 1 wherein said core has a circular bend flexibility of less than about 10 N.

8. An absorbent article according to claim 1 wherein said absorbent article further has a dry caliper less than about 4 mm.

* * * * *